(12) United States Patent
Hall

(10) Patent No.: US 8,167,618 B2
(45) Date of Patent: *May 1, 2012

(54) ARRANGEMENT FOR USING OSTEOINDUCTIVE OR BIOACTIVE MATERIAL TO INDUCE BONE AND/OR INCREASE THE STABILITY OF IMPLANTS IN THE JAW BONE, AND AN IMPLANT INTENDED FOR THIS PURPOSE

(75) Inventor: Jan Hall, Gothenburg (SE)

(73) Assignee: Nobel Biocare AB (publ), Gothenburg (SE)

( * ) Notice: Subject to any disclaimer, the term of this patent is extended or adjusted under 35 U.S.C. 154(b) by 52 days.

This patent is subject to a terminal disclaimer.

(21) Appl. No.: 12/210,899

(22) Filed: Sep. 15, 2008

(65) Prior Publication Data

US 2009/0047631 A1    Feb. 19, 2009

Related U.S. Application Data

(62) Division of application No. 10/521,743, filed as application No. PCT/SE03/01106 on Jun. 26, 2003, now abandoned.

(30) Foreign Application Priority Data

Jul. 25, 2002    (SE) ...................................... 0202315

(51) Int. Cl.
*A61C 8/00*    (2006.01)
(52) U.S. Cl. ...................................................... 433/173
(58) Field of Classification Search .................. 433/172, 433/173, 174, 175, 215
See application file for complete search history.

(56) References Cited

U.S. PATENT DOCUMENTS

| | | | |
|---|---|---|---|
| 4,738,623 A | 4/1988 | Driskell | |
| 5,344,457 A | 9/1994 | Pilliar et al. | |
| 5,700,479 A * | 12/1997 | Lundgren | 424/435 |
| 5,759,033 A | 6/1998 | Elia | |
| 6,193,516 B1 * | 2/2001 | Story | 433/173 |
| 6,214,049 B1 | 4/2001 | Gayer et al. | |
| 6,244,868 B1 * | 6/2001 | Schappert | 433/173 |
| 6,325,627 B1 * | 12/2001 | Ashman | 433/173 |
| 6,382,976 B1 * | 5/2002 | Wagner | 433/174 |
| 6,413,089 B1 * | 7/2002 | Ashman et al. | 433/174 |

* cited by examiner

*Primary Examiner* — Ralph Lewis
(74) *Attorney, Agent, or Firm* — Connolly Bove Lodge & Hutz LLP

(57) ABSTRACT

The stability of an implant (5) which is fitted in a jaw bone hole created by tooth root extraction is increased using osteoinductive material. Bone formation in the space between the implant and the bone wall is also stimulated. In an initial stage, the implant is anchored or fitted in the hole. With its outer parts (5a) the implant extends into a part (4a) of the hole which has a cross-sectional area exceeding the crossectional area of the outer parts (5a) of the implant. The soft tissue of the jaw bone, with possible periosteum, covers the implant and the space to form a closed space (4a). The bioactive material consists of growth-stimulating substances (GSS) arranged on the implant. In a stage of incorporation, GSS passes outward into body fluid which has penetrated into the closed space and interacts with cells present in the fluid so that new bone is formed around the outer pats (5a) of the implant. The invention also relates to a use and to an implant. The invention also simplifies the handling of implants.

10 Claims, 3 Drawing Sheets

Figure 1:
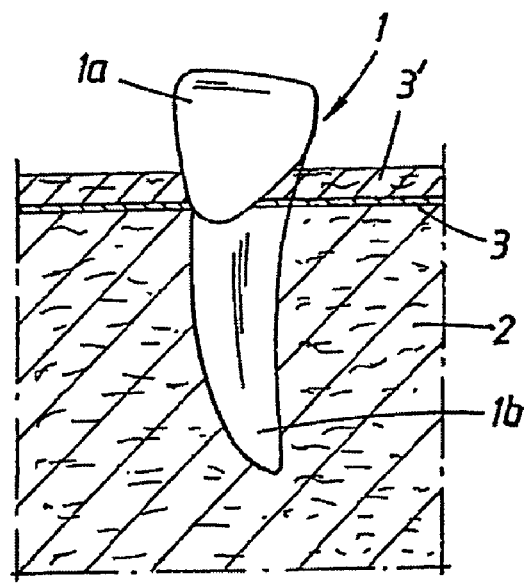

ARRANGEMENT FOR USING OSTEOINDUCTIVE OR BIOACTIVE MATERIAL TO INDUCE BONE AND/OR INCREASE THE STABILITY OF IMPLANTS IN THE JAW BONE, AND AN IMPLANT INTENDED FOR THIS PURPOSE

This application is a divisional of application Ser. No. 10/521,743 filed Jan. 19, 2005 now abandoned, which is a national stage of PCT/SE03/01106 filed Jun. 26, 2003, claiming priority from Swedish application number 0202315-8 filed Jul. 25, 2002, the entire disclosures of which are herein incorporated by reference in their entireties.

The present invention relates to an arrangement for using osteoinductive material to induce bone and/or increase the stability of implants applied in jaw bone holes which have been created by tooth root extraction. In an initial stage, the implant is anchored or fitted in the hole via its inner parts, and with its outer parts it extends into a part of the hole which has a cross-sectional area exceeding the cross-sectional area of the outer parts of the implant. The outer parts of the hole, the implant and the soft tissue of the jaw bone, with or without periosteum, constitute a closed space at said outer parts.

The invention also relates to a use in a jaw bone hole created by tooth root extraction which has given the hole a cross-sectional area at the outer parts of the hole which exceeds the cross-sectional area of the hole at its inner parts.

The invention also relates to an implant which can be fitted in a jaw bone hole created by tooth root extraction and arranged with its outer parts extending into a part of the hole which has a cross-sectional area exceeding the cross-sectional area of the outer parts.

The terms "inner" and "outer" parts refer to the locations in the longitudinal direction, i.e. the inner parts are located farthest into the jaw bone, and the outer parts are situated at outer parts of the jaw bone. Said terms thus do not relate, for example, to parts of the implant lying on the outside or on the inside.

Reference may be made in this connection to patent applications SE 9901972-1 and WO 00/72778 filed by the same Applicant and with the same inventor as in the present patent application.

Reference may also be made to the article published by, inter alia, the inventor of the present patent application and entitled "Properties of a New Porous Oxide Surface oh Titanium Implants, Volume 1: The Oxidized Titanium Surface, Applied Osseointegration Research".

In connection with jaw bone holes of said type, it is already known to fit implants and to fill the space situated between the implant and the outer parts of the jaw bone hole with substrates of various types, for example substrate in the form of autologous bone, allogenic bone, xenografts, or synthetic material, for example in the form of or comprising calcium phosphates (e.g. hydroxylapatite). The space thus filled with substrate is sewn closed or covered over with the soft tissue, possibly in combination with some form of covering membrane. A characteristic of the substrate is that it is resorbable to a greater or lesser extent and is gradually replaced by bone. Doses of different substrates are available on the market from a number of companies operating on the market. Reference is made quite generally to these known substrates.

It has been found, however, that the known substrates are not always able to satisfy the strict requirements placed on dental fittings of the type in question. The requirements also vary considerably from one person to another, which means that it is difficult to develop general and satisfactory methods and arrangements for stabilizing the implants sufficiently and in an acceptable way.

The present invention aims to solve these problems among others and proposes a novel use of implants which in one embodiment can be of a type known per se. The implants are in this case of the type which in some way or another has been provided with growth-stimulating substance(s) (GSS) which in a known manner is/are able to generate new bone, i.e. in this case jaw bone, in cooperation with cells, for example stem cells, which are found in the body and occur for example in body fluid formed in the cavities of the body which have been subjected to an intervention, for example in the form of tooth extraction. By introducing said GSS into cell-containing body fluids, the interaction between GSS and the cells can initiate formation of new bone or new bone parts. In accordance with the invention, this gives a much improved anchoring function for the implant in question, which can thus be anchored with much improved stability compared to the previously known techniques according to the above.

It is also known that the space in the jaw bone is often replaced with soft tissue instead of bone, which does not satisfy the requirements set. The invention also intends to solve this problem.

There is also a need to simplify the tooth replacement work carried out by the surgeon, dentist or other person performing treatment. When using bone from the patient's iliac crest, for example, problems may arise because the process of obtaining bone from the iliac crest can be quite extensive and painful. In some countries there are also restrictions which mean that a person providing treatment in the area of dentistry cannot carry out any interventions on other parts of the body. This can therefore entail the cooperation of a number of different specialists, which considerably increases the costs of the fitting and replacement work.

The feature which can principally be, regarded as characterizing an arrangement according to the invention is, inter alia, that the bioactive material consists of GSS arranged on or in the implant, for example on its outer surface or outer thread, at its outer parts. In a stage of incorporation of the implant, said GSS passes outward into body fluid which has penetrated or is penetrating from the surrounding tissue and periosteum into the aforementioned closed space and interacts with cells present in the fluid, which leads to formation of new bone around said outer parts of the implant.

In one embodiment of the inventive concept, GSS can be arranged in principle only at or on said outer parts of the implant. GSS can also be arranged as one or more layers lying on the outside of the implant's outer part or outer thread. GSS can also be arranged together with one or more layers of, for example, calcium phosphate(s). The implant can be provided in a manner known per se with a reservoir function for GSS, and this can consist of porous outer layers and/or oxide layers arranged at least at said outer parts of the implant. In one embodiment, GSS can also be combined with bone substitute of known type, which can be applied as layers directly on the surface or thread.

The feature which can principally be regarded as characterizing a use according to the invention is that, for new production of bone in a space closed with periosteum between an implant and the wall of the hole in the jaw bone, use is made of GSS grafted onto the outer parts of the implant and passing outward into cell-containing body fluid which penetrates or has penetrated into the space.

Further characteristics of the subject matter of the invention are set out in the attached dependent claims. As regards implants, there is a need to be able to abandon the conventional production methods for implants and instead be able to cast or mill these from a blank. The implant must be able to have a shape, corresponding to the jaw bone hole in questions so that it is possible to anchor the implant without having to use threads, for example, in the implant and jaw bone. The invention also solves this problem.

The feature which can principally be regarded as characterizing an implant according to the invention is, inter alia, that it is provided with growth-stimulating substance(s) (GSS) interacting with cells in body fluid so that new bone is formed. In addition, the implant can have its inner parts configured as tooth root shapes. Further developments of the implant are set out in the attached dependent claims.

By means of what has been proposed above, a considerably improved anchoring of the implant in the jaw bone hole is achieved, despite the fact that from the start the latter has a greater cross-sectional area than the actual implant at the outer parts. Using the formed closed space, a body fluid space can be formed and an effective production of new bone is achieved in an optimum manner with the correct amount of GSS in relation to the volume of the space. The presently practiced or proposed technique for applying GSS to implants can be used advantageously and in this way the front line of the new technique can be pushed forward considerably. The GSS used can be matrix molecules, growth factors, differentiation factors, peptides with growth-stimulating properties, etc.

Figure 2:
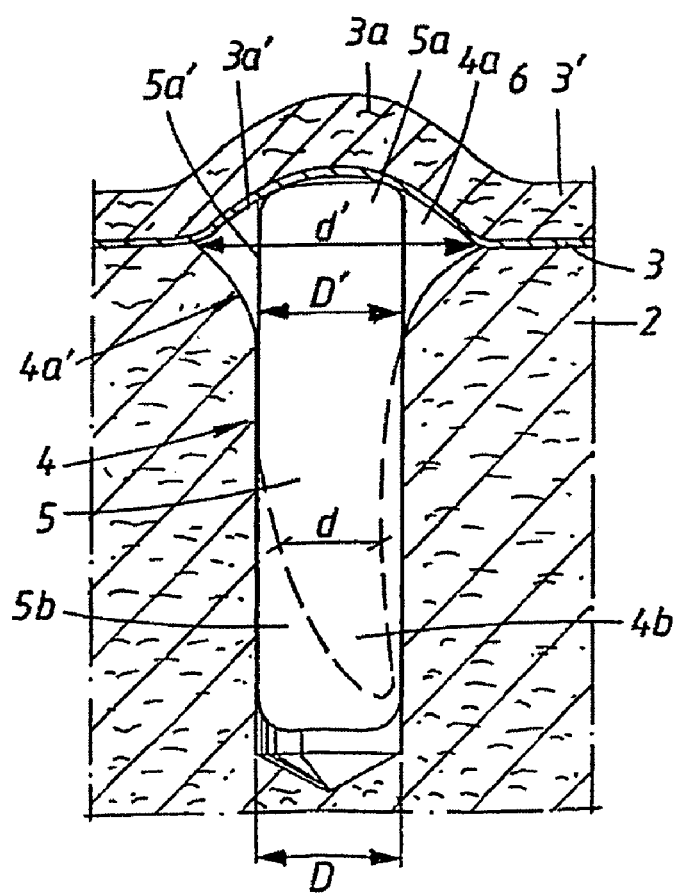
Figure 3:
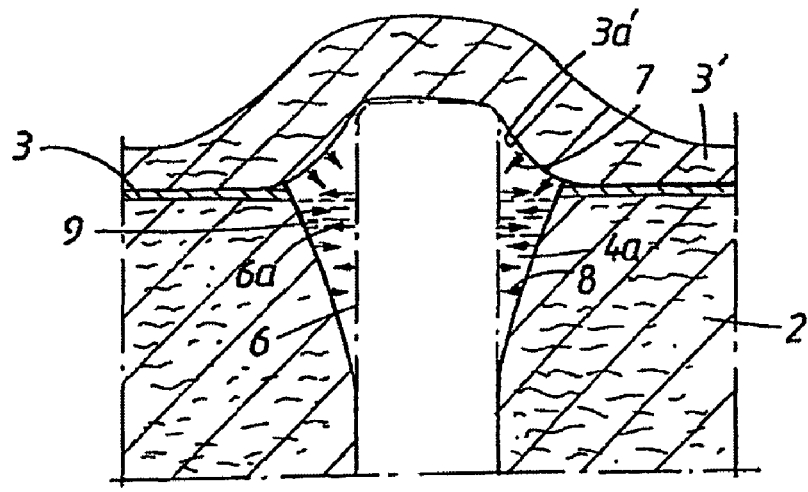
Figure 4:
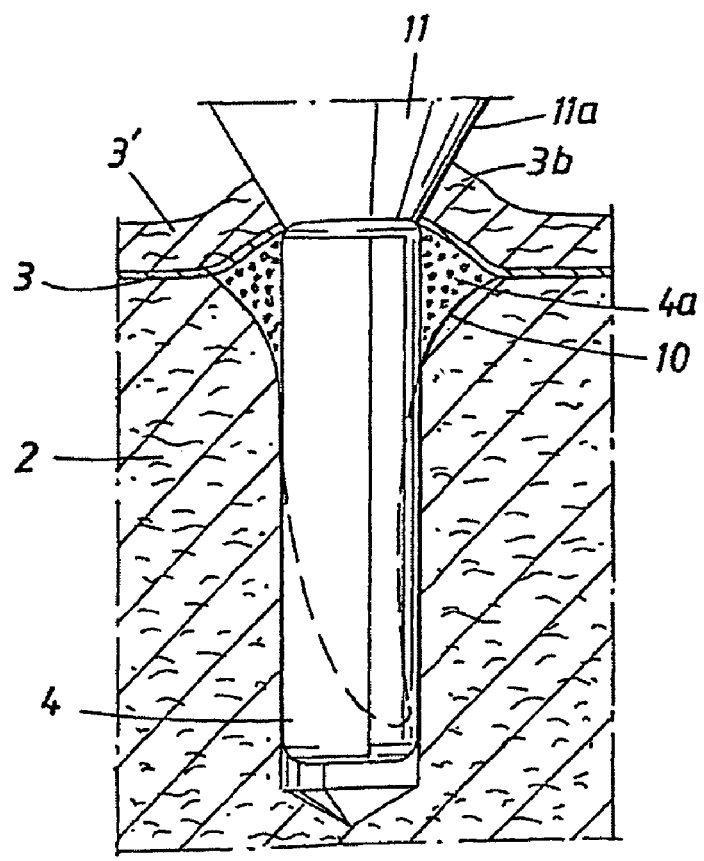
Figure 5:
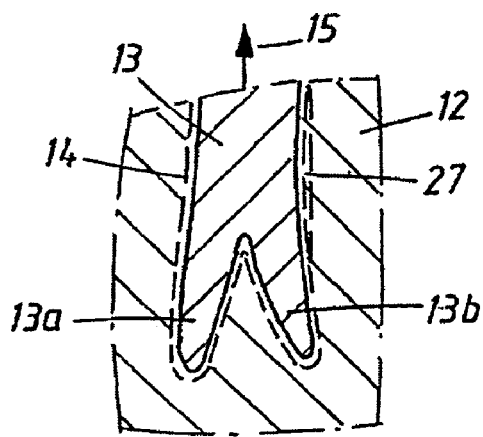
Figure 7:
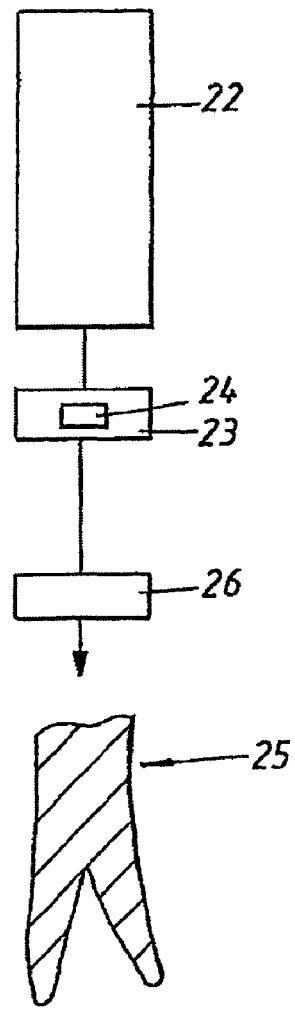
Figure 6:
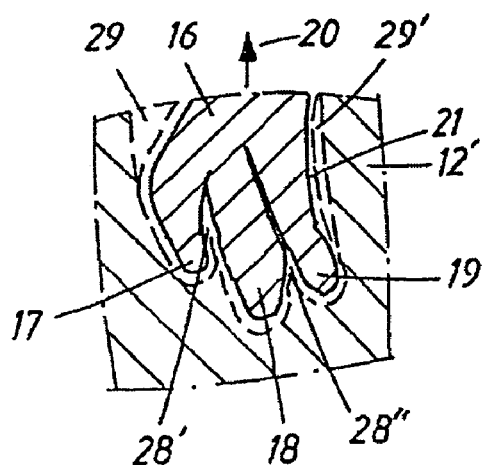

A presently proposed embodiment of an arrangement, a use and an implant according to the invention will be described below with reference to the attached drawings, in which FIG. 1 shows a vertical view of a tooth in a jaw bone with soft tissue, which tooth is intended to be removed in its entirety in a manner known per se, i.e. together with its tooth root part, FIG. 2 shows a vertical section of a jaw bone hole present after extraction of the tooth according to FIG. 1, in which an implant has been fitted, and the soft tissue has been pulled over the implant and a space between the implant and the jaw bone hole, FIG. 3 shows an enlarged vertical view of parts of the implant, the jaw bone and the soft tissue according to FIG. 2, and where GSS is released from the outer parts of the implant and body fluid with cells, for example stem cells, is released from the jaw bone and the periosteum lying under the soft tissue, FIG. 4 shows a vertical view of bone newly formed by GSS in the space between the implant and the jaw bone, and parts of the soft tissue, and FIGS. 5-7 show diagrammatically, in vertical views, different configurations of the jaw bone hole and the implant at the inner parts, and the principle of production of the implants.

In FIG. 1, a tooth is shown symbolically by 1. The tooth is fitted in a jaw bone 2 which at its top surface is provided with soft tissue (gingiva) 3' and periosteum 3, which are indicated symbolically. The figure also indicates, with 1a, the part of the tooth projecting above the soft tissue 3'. The tooth root is shown by 1b.

In FIG. 2, reference number 4 indicates a jaw bone hole which is present when the tooth according to FIG. 1 has been completely extracted, i.e. with the root 1b and all. The shape of the jaw bone hole largely follows the shape of the tooth 1 (see FIG. 1) in the jaw bone. The hole thus has a widened part 4a at its outer parts and a relatively narrow part 4b at its inner parts. The hole's appearance thus varies as a function of the tooth which is to be extracted, but a characteristic of the jaw bone hole is that it is narrower at its inner parts 4b than at its outer parts 4a. In the figure, an implant 5 has been fitted in the jaw bone hole. The implant has outer parts 5a, meaning those parts which are situated farthest outward in relation to the dentine. In addition, the implant has inner parts 5b, representing those parts situated farthest into the dentine 2. The implant has a diameter D which, at the inner parts 5b, exceeds the diameter d of the jaw bone hole. The implant can be of a type known per se and can, for example, be of the self-tapping type, cf. the implants sold on the market by Nobel Biocare. In this case, the implant is tapered at said inner parts 5b, although this is not specifically indicated in FIG. 2. The tapered part at the end of the implant also exceeds said diameter d. At the upper parts of the implant, the implant's diameter D' is smaller than the diameter d' of the jaw bone hole. The jaw bone hole thus widens outward/upward (in the figure) and can have a cone shape along parts or all of its length. At said outer parts 4a, the space between the outer surface or outer thread 5a' of the implant and the wall 4a' of the jaw bone hole is considerable. At its broadest part, the cross-sectional area of the jaw bone hole can assume twice the diameter of the cross-sectional area of the implant. In accordance with the concept of the invention, a closed space 4a will be present between the outer surface 5a' of the implant and the hole wall 4a' and an underside or bottom surface of part of the soft tissue, with or without periosteum, which is drawn over the space and the implant and sewn together, for example, so that the soft tissue and possibly the periosteum 3a, if present, cover the implant and the space, and in this way a closed space 4a is formed. In the present case, periosteum 3a is assumed to be present under the soft tissue and its bottom surface is indicated by 3a'. In accordance with what is described below, at least that part of the implant (its outer parts) located in the closed space 9a is provided with grafted GSS in accordance with what is described below.

FIG. 3 shows how GSS 6 is released from the implant surface and passes outward into the space 4a. Directional arrows for this are indicated by 6a. It is known that body fluid collects in the space 4a. Cells, for example stem cells from the lower surface 3a' of the periosteum, are indicted by the arrows 7, and cells from the jaw bone 2 are indicated by the arrows 8. The accumulation of body fluid is symbolized by 9. The body fluid contains cells with which the GSS interacts, so that new bone is formed in the space 4a. This process depends on the amount of GSS on the implant surface parts, the amount and type of cells, and the size of the space 4a, i.e. the amount of body fluid. The periosteum is a source of stem cells which greatly stimulate said formation of new bone in the case where GSS consists of differentiation factors such as bone morphogenetic proteins (BMP).

FIG. 4 shows the situation where the process of new bone formation, i.e. the process of incorporation of the implant, is completed. The newly formed bone in principle fills the entire space 4a. The implant 5 has been provided with a diagrammatically indicated attachment 11 for a dental fixture which in principle can replace the upper part 1a of the extracted tooth, cf. FIG. 1. The fitting operation can be carried out in a manner known per se. The soft tissue with periosteum 3', 3 has been attached to an outer surface 11a of the fixture and bears via a part 3b against the outer surface 11a in question.

Thus, an implant known per se can be used in the tooth replacement function. An implant which in a known manner or a novel manner is provided with grafted or otherwise applied GSS is used in the jaw bone hole in question. The implant can be screwed into the hole using the self-tapping principle. Alternatively, the hole can be threaded to match an implant. This pre-threading can also take place in a manner known per se. The newly formed bone contributes to strong stabilization of the implant in the jaw bone hole. The amount of GSS can in this case be related to the volume of the closed space, the clinical situation and/or the tooth which is to be replaced with the implant/dental construction, etc. The hole around the implant can be covered with a membrane or a protective part of a type known per se. The implant is preferably made of titanium but can consist of another biocompatible material, for example ceramic.

In FIG. 5, a jaw bone is indicated diagrammatically by 12. A tooth in the jaw bone is indicated by 13 and the tooth is in this case of the type which has two root parts 13a and 13b. The tooth extends in the jaw bone hole 14 which is shown with an overdimensioned gap for reasons of clarity. The tooth can be extracted from the jaw bone in the direction of arrow 15. The same applies to FIG. 5 which shows an alternative design of the tooth root.

FIG. 6 shows the lower parts of a tooth 16 provided with three root parts 17, 18 and 19. The jaw bone is in this case indicated by 12'. The tooth 16 in question can be extracted from the jaw bone in the direction of arrow 20. The hole 21 in the jaw bone for this tooth is shown with an overdimensioned gap for reasons of clarity.

Upon extraction of the tooth 13 according to FIG. 5 together with the root and all, the jaw bone hole 14 acquires a shape corresponding to that of the tooth. In accordance with FIG. 7, an appliance 22 is used to define or image the jaw bone hole 14 in FIG. 5 when the tooth 13 has been extracted. An imaging technique known per se can be used, for example X-ray, computed tomography, etc. With the appliance 22, the surgeon, the dentist or other person performing treatment is given an image of the shape of the jaw bone hole 14. The shape is assigned a representation in an appliance 23 which can be part of a computer installation known per se. The representation is symbolized by 24 and can be used as a basis for production of an implant 25 which is intended to be placed in the jaw bone hole 14 in question (see FIGS. 5 and 5a). The fitting operation can be carried out in such a way that the implant can be applied with relatively little clearance in the jaw bone hole. In the present case, the implant 25 has a design which, upon application of the implant in the jaw bone hole, means that the hole wall springs aside and then back to a position corresponding to the position of the tooth 13 in FIG. 5. Alternatively, the implant can be made to some extent resilient in those parts which upon application are intended to match narrowing parts in the jaw bone hole. Alternatively, the inner parts of the tooth root extend in such a way that they together have cross-sectional areas which are smaller than the cross-sectional area or cross-sectional areas of above parts of the jaw bone hole. The implant 25 in question can be produced using production equipment 26 of the PROCERA type. The implant can be milled, cast, or produced in some other way. The implant can be given an optimum geometric configuration so that the load on the implant is correctly distributed.

It also lies within the possibilities of the invention that the line of the jaw bone hole can be acted upon using tools, for example drilling tools, so that wider parts situated at the bottom can easily match passages in the hole which have been narrower from the start. In FIG. 5, such working is indicated by 27. The space initiated in this way by the recessing or working 27 around the fitted implant can be used as a closed space for new bone formation in accordance with what has been described above. Such working of jaw bone holes can be carried out in different ways from case to case.

Figure 5A:
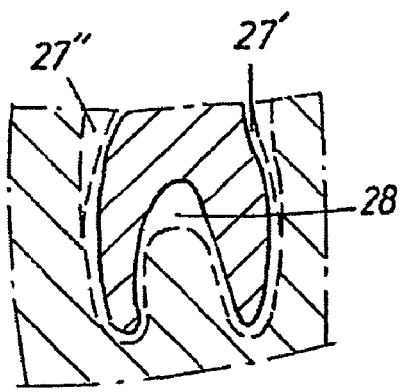

FIG. 5a shows an alternative double root configuration. In this case, the sides of the jaw bone hole have been worked twice at 27' and 27", and the area between the original positions of the two roots has been worked at 28. The space 28 can be used as a closed space for new bone formation.

In FIG. 6, the spaces 28' and 28" have been formed at the lower parts of the tooth root. In accordance with the above, these spaces 28' and 28" can be used as closed spaces for new bone formation. It will be appreciated that in cases where there is no resiliency function in the jaw bone or implant, said working can allow the tooth roots belonging to the tooth in question to be simulated to a very high degree when producing the implant in question, i.e. the implant 25 in FIG. 7. The root formations according to FIGS. 5a and 6 can also be completed in a relatively simple manner with working(s) 27', 27" and 29, 29', respectively, permitting application of an implant with a configuration which corresponds to the design of the tooth root arrangement according to FIGS. 5a and 6. The space 29 is also used as a closed space for new bone formation. GSS can be applied in a known manner as a thin skin (a few nanometers thick) on the actual outer surface.

The invention is not limited to the embodiment shown above by way of example, and instead it can be modified within the scope of the attached patent claims and the inventive concept.

Reference may be made here to patent applications submitted to the Swedish patent office on the same day as the present patent application and by the same Applicant and inventor. Said applications have the following titles:

a) "Arrangement for using bioactive material to build up a bone-based lateral support for implants in the jaw bone".
b) "Arrangement for implants bearing growth-stimulating substance or substances, and one such implant".
c) "Arrangement of two or more implants provided with growth-stimulating substance(s)".
d) "Arrangement for increasing the stress resistance of implants, and one such implant".

The invention claimed is:

1. A method for fitting an implant into a jaw bone hole having adjacent soft tissue, the jaw bone hole comprising an inner hole part at the distal end of the hole and an outer hole part at the proximal end of the hole with respective inner and outer hole diameters, wherein said inner and outer hole diameters are different from each other, the implant comprising an inner implant part having an inner implant diameter that is greater than the inner hole diameter, an outer implant part having an outer implant diameter that is lesser than the outer hole diameter, and at least one growth stimulating substance (GSS) disposed on an outer surface of said outer implant part prior to insertion into the jaw bone, which at least on GSS is configured to be released from the implant to interact with at least bodily fluid to form new bone, comprising:
   anchoring the implant into said formed jaw bone hole by fitting the inner implant part into the inner jaw bone hole;
   forming a closed space by covering said formed jaw bone hole with the soft tissue adjacent the jaw bone hole, wherein said formed closed space is defined by at least the soft tissue, an outer surface of the outer implant part, and the outer hole part without any substrate or substitute in the closed space; and
   allowing the GSS disposed on the implant to be released into said formed closed space and interact with at least one bodily fluid disposed therein to form new bone growth.

2. The method of claim 1, wherein said forming a jaw bone hole comprises drilling the jaw bone.

3. The method of claim 1, wherein said forming a jaw bone hole comprises extracting a tooth from the jaw bone.

4. The method of claim 1, wherein said forming a closed spaced by covering said formed jaw bone hole further comprises drawing said soft tissue over said formed jaw bone hole in order to sealingly close the formed jaw bone hole.

5. The method of claim 4, wherein said soft tissue comprises periosteum.

6. The method of claim 4, further comprising sewing said drawn tissue together to sealingly close the formed jaw bone hole.

7. The method of claim 1, wherein said allowing the GSS disposed on the implant to be released further comprises allowing the GSS to interact with cell-containing body fluid penetrating into said formed closed space.

8. The method of claim 1, wherein said GSS comprises one of at least matrix molecules, growth factors, differentiation factors, and peptides with growth-stimulating properties.

9. The method of claim 5, wherein said GSS comprises at least one differentiation factor.

10. The method of claim 9, wherein said differentiation factor comprises BMP.

* * * * *